United States Patent
Carns et al.

(10) Patent No.: US 7,437,952 B2
(45) Date of Patent: Oct. 21, 2008

(54) SHROUDED BODY FLOW METER ASSEMBLY

(75) Inventors: James A Carns, Wichita, KS (US); Theron L Cutler, Wichita, KS (US); Mark A Shelly, Bel Aire, KS (US)

(73) Assignee: The Boeing Company, Chicago, IL (US)

( * ) Notice: Subject to any disclaimer, the term of this patent is extended or adjusted under 35 U.S.C. 154(b) by 199 days.

(21) Appl. No.: 11/450,925

(22) Filed: Jun. 9, 2006

(65) Prior Publication Data

US 2006/0278017 A1  Dec. 14, 2006

Related U.S. Application Data (60) Provisional application No. 60/689,677, filed on Jun. 10, 2005.

(51) Int. Cl.
   *G01F 1/05* (2006.01)
   *G01F 15/00* (2006.01)
(52) U.S. Cl. ............................ 73/861.79; 73/861.77
(58) Field of Classification Search . 73/861.25–861.33, 73/861.77–861.79
   See application file for complete search history.

(56) References Cited

U.S. PATENT DOCUMENTS

| | | | |
|---|---|---|---|
| 724,675 A | | 4/1903 | Decker |
| 2,475,635 A | | 7/1949 | Parsons |
| 2,668,066 A | | 2/1954 | Stadelhofer |
| 3,043,141 A | | 7/1962 | Waugh et al. |
| 3,680,378 A | * | 8/1972 | Aurilio et al. ............ 73/861.77 |
| 3,686,948 A | | 8/1972 | Lahaye |
| 3,735,637 A | * | 5/1973 | Penet ........................ 73/861.84 |
| 3,928,903 A | | 12/1975 | Richardson et al. |
| 4,012,958 A | * | 3/1977 | Taylor ....................... 73/861.77 |
| 4,013,953 A | * | 3/1977 | Skala ......................... 73/861.77 |
| 4,109,526 A | * | 8/1978 | Rosso ........................ 73/861.78 |
| 4,149,739 A | | 4/1979 | Morris |
| 4,408,498 A | * | 10/1983 | Heath ........................ 73/861.79 |
| 4,694,865 A | | 9/1987 | Tauschmann |
| 4,929,000 A | | 5/1990 | Annestedt, Sr. |
| 5,388,466 A | * | 2/1995 | Teunissen ................. 73/861.33 |
| 5,433,118 A | * | 7/1995 | Castillo .................... 73/861.77 |
| 5,449,203 A | | 9/1995 | Sharp |
| 5,449,204 A | | 9/1995 | Greene et al. |
| 5,782,263 A | * | 7/1998 | Isaacson, Jr. et al. ..... 137/487.5 |
| 5,831,176 A | * | 11/1998 | Morgenthale et al. .... 73/861.77 |
| 6,119,528 A | * | 9/2000 | Genack ..................... 73/861.12 |
| 6,302,448 B1 | | 10/2001 | Van Der Meer et al. |
| 6,428,054 B1 | | 8/2002 | Zappa et al. |
| 6,782,765 B2 | * | 8/2004 | Dussault ................... 73/861.79 |

(Continued)

FOREIGN PATENT DOCUMENTS

DE  2744674  4/1979

*Primary Examiner*—Harshad Patel
(74) *Attorney, Agent, or Firm*—Harness, Dickey & Pierce, P.L.C.

(57) ABSTRACT

A shrouded body flow meter assembly includes an inner fluid-conducting conduit disposed in a spaced relation from and within an outer conduit. The shrouded flow meter assembly can be connected to other shrouded fluid-conducting apparatus and/or used to replace sections of a shrouded fluid-conducting apparatus system. The shrouded flow meter assembly maintains the integrity of the inner fluid-conducting conduits and outer conduits of the shrouded fluid-conducting apparatus.

17 Claims, 4 Drawing Sheets

U.S. PATENT DOCUMENTS

| | | | |
|---|---|---|---|
| 6,848,720 B2 * | 2/2005 | Carns et al. | 285/123.15 |
| 6,854,342 B2 * | 2/2005 | Payne et al. | 73/861.79 |
| 6,929,018 B2 * | 8/2005 | Shepard et al. | 137/1 |
| 7,111,520 B2 * | 9/2006 | Payne et al. | 73/861.79 |
| 7,398,697 B2 * | 7/2008 | Allen et al. | 73/800 |
| 2004/0026922 A1 | 2/2004 | Carns et al. | |
| 2005/0120534 A1 | 6/2005 | Carns et al. | |
| 2007/0051406 A1 * | 3/2007 | Carnes | 137/312 |

* cited by examiner

SHROUDED BODY FLOW METER ASSEMBLY

CROSS-REFERENCE TO RELATED APPLICATIONS

This application claims the benefit of U.S. Provisional Application No. 60/689,677, filed on Jun. 10, 2005. The present application is generally related to subject matter disclosed in co-filed applications "Aerial Refueling System," U.S. patent application Ser. No. 11/313,190, filed Dec. 20, 2005; "Shrouded Fluid-Conducting Apparatus," U.S. patent application Ser. No. 11/150,853, filed Jun. 10, 2005; "Redundant Seal Fitting—Fluid Carrying Apparatus" (Boeing Docket No. 05-0564); "Surge Pressure Reducing Hose Assembly" (Boeing Docket No. 05-0565); and "Manifold Mounting—Load Carrying Apparatus, Infinitely Adjustable" (Boeing Docket No. 05-0566); "Ball Joint Assembly—Fluid Conducting Apparatus, Fully Articulating" (Boeing Docket No. 05-0567). The disclosures of the above applications are incorporated herein by reference.

FIELD OF THE INVENTION

The present invention relates generally to flow meter assemblies and, more particularly, to shrouded flow meter assemblies.

BACKGROUND OF THE INVENTION

According to Federal Aviation Administration (FAA) regulations, fuel lines (e.g., manifolds, conduits) that conduct or transport fuel through areas classified by the FAA as "ignition zones" (e.g., pressurized areas) must be shrouded and capable of being drained. The applicable sections of the FAA requirements relative to fuel lines in aircraft ignition zones for transport category airplanes are contained in 14 C.F.R. Part 25, the pertinent parts of which are set forth below.

For example, Section 25.855 states in pertinent part that "for each cargo and baggage compartment not occupied by crew or passengers . . . no compartment may contain any controls, wiring, lines, equipment, or accessories whose damage or failure would affect safe operation, unless those items are protected so that . . . they cannot be damaged by the movement of cargo in the compartment, and . . . their breakage or failure will not create a fire hazard." Section 25.863 states in pertinent part that "in each area where flammable fluids or vapors might escape by leakage of a fluid system, there must be means to minimize the probability of ignition of the fluids and vapors, and the resultant hazards if ignition does occur." Section 25.901 states in pertinent part that "for each power plant and auxiliary power unit installation, it must be established that no single failure or malfunction or probable combination of failures will jeopardize the safe operation of the airplane except that the failure of structural elements need not be considered if the probability of such failure is extremely remote." Section 25.967 states in pertinent part that "each fuel tank must be isolated from personnel compartments by a fumeproof and fuelproof enclosure."

To summarize, the FAA regulations ensure that no single failure will jeopardize safe operation of the aircraft, as would be the case if single-wall fuel manifolds were used in aircraft "ignition zones." That is, a leak or rupture in a single-wall fuel manifold would allow fuel to enter the "ignition zone", which could result in catastrophic event were the fuel to ignite or explode.

To comply with the FAA shrouded fuel line requirements, a shrouded fluid-conducting apparatus utilizing an inner conduit disposed within an outer conduit has been employed. The monitoring and/or measuring of properties of the fluid flowing through the shrouded fluid-conducting apparatus, however, have not been addressed. Thus, it would be advantageous to provide an assembly and/or method of monitoring and/or measuring properties of a fluid flowing through a shrouded fluid-conducting apparatus that meets and/or exceeds the FAA regulations.

SUMMARY OF THE INVENTION

In one aspect of the present invention, a shrouded flow meter is disclosed. The shrouded flow meter includes a fluid tight inner conduit operable to conduct a fluid therethrough. A fluid tight outer conduit is disposed over the inner conduit with a space therebetween. A detector is attached to the outer conduit and is operable to sense a signal indicative of a characteristic of a fluid in the inner conduit. The detector is isolated from direct contact with the fluid in the inner conduit.

In another aspect of the present invention, a method of determining a characteristic of fluid within an inner conduit of a shrouded fluid-conducting apparatus is disclosed. The method includes: (1) locating a detector proximate the inner conduit of the shrouded fluid-conducting apparatus while maintaining an integrity of the inner conduit; (2) sensing a signal with said detector based on a fluid within the inner conduit; and (3) converting the sensed signal into a characteristic of the fluid within the inner conduit.

The features, functions, and advantages can be achieved independently in various embodiments of the present inventions or may be combined in yet other embodiments.

BRIEF DESCRIPTION OF THE DRAWINGS

The present invention will become more fully understood from the detailed description and the accompanying drawings, wherein.

DETAILED DESCRIPTION OF THE PREFERRED EMBODIMENT

The following description of the preferred embodiment is merely exemplary in nature and is in no way intended to limit the invention, its application, or uses. As used herein, the term module refers to an application specific integrated circuit (ASIC), an electronic circuit, a processor (shared, dedicated or group) and memory that execute one or more software or firmware programs, a combinational logic circuit, or other suitable components that provide the described functionality.

The following description of the preferred embodiments is merely exemplary in nature and is in no way intended to limit the invention, its application, or uses. For example, it is anticipated that the invention will be applicable to any of a wide range of aircraft (e.g., but not limited to, fighter jets, commercial jets, private jets, propeller powered airplanes, among others) regardless of the manner in which the aircraft is piloted (e.g., directly, remotely, via automation, or in a combination thereof, among others). Indeed, the present invention need not even be limited to aircraft. Accordingly, the specific references to aircraft herein should not be construed as limiting the scope of the present invention. In addition, it is also anticipated that the invention will be applicable to any of a wide range of fluids, e.g., gases and liquids, regardless of whether the fluid is being used as a fuel. Accordingly, the specific references to fuel, gases, or liquids herein should not be construed as limiting the scope of the present invention.

In addition, certain terminology will also be used in the following description for the purpose of reference only, and thus are not intended to be limiting. For example, terms such as "upper", "lower", "above", and "below" refer to directions in the drawings to which reference is made. Terms such as "front", "back", "rear", and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

Figure 1:
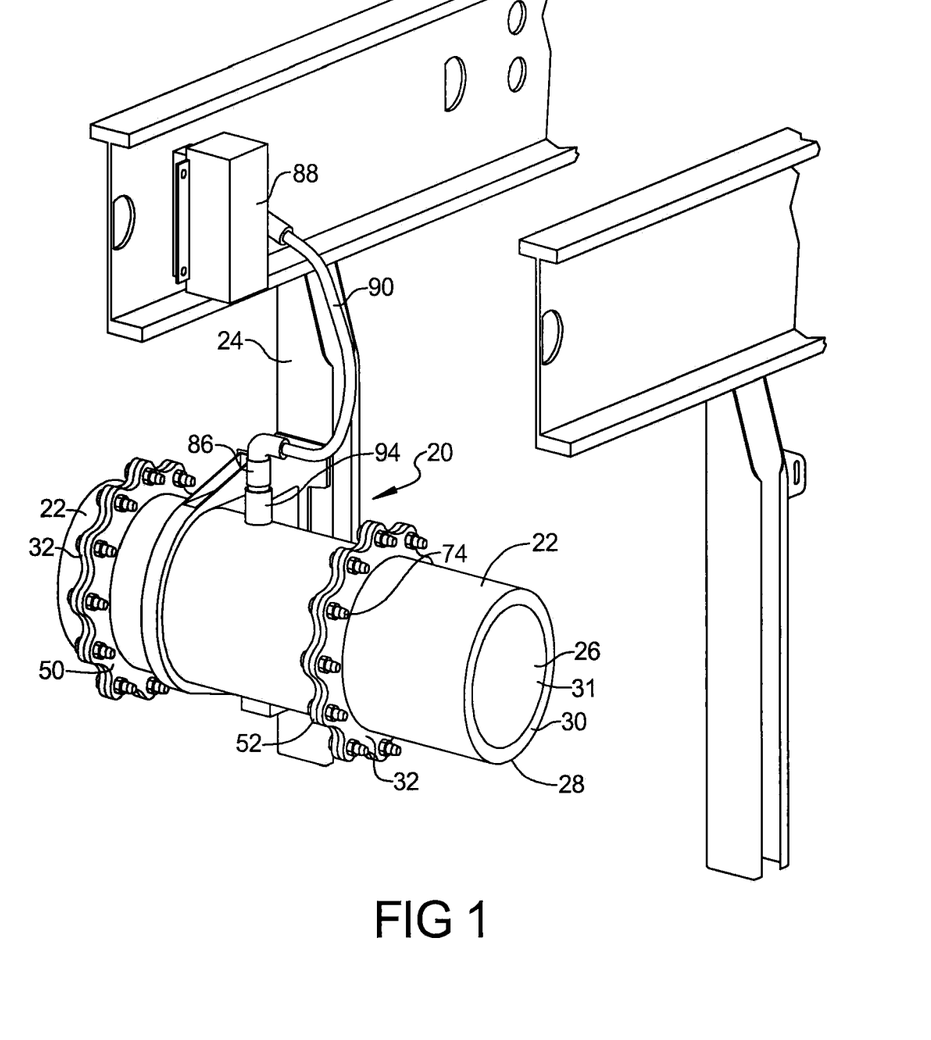
FIG. 1 is a perspective view of a portion of a shrouded (double-walled) fluid-conducting apparatus connected to a shrouded flow meter assembly according to the principles of the present invention.

Referring to FIG. 1, a shrouded flow meter assembly 20 according to the principles of the present invention is shown installed inline with shrouded fluid-conducting apparatuses 22 and attached to a framing member 24. Shrouded fluid-conducting apparatus 22 can take many forms and variations. Shrouded fluid-conducting apparatus 22 includes an inner fluid-conducting conduit 26 disposed within and spaced apart from an outer conduit 28. Outer conduit 28 includes a lumen (cavity or channel) 30 that is sized to receive inner conduit 26. Inner conduit 26 includes a lumen (cavity or channel) 31 that allows for a fluid (e.g., gases and liquids) to flow through inner conduit 26. Outer conduit 28 shrouds inner conduit 26 to contain any fluid leaking from inner conduit 26 and prevents the leaking fluid from reaching the compartment in which shrouded fluid-containing apparatus 22 is being used. Accordingly, inner and outer conduits 26 and 28 must both fail before a fluid being conducted through inner conduit 26 can reach the compartment or space in which shrouded fluid-conducting apparatus 22 is being used. Shrouded fluid-conducting apparatus 22 thus allows a fluid to be conducted through inner conduit 26 under a double failure condition.

Support members (not shown) support inner fluid-conducting conduit 26 within outer conduit 28. Inner conduit 26 may be inclined to move or shift within outer conduit 28 while a fluid is being conducted through inner conduit 26. The support members can reduce and possibly prevent the movement of inner conduit 26 within outer conduit 28. In other words, the support members can hold or keep inner conduit 26 substantially stationary with respect to outer conduit 28. Additionally, the support members may also allow for loads to be transferred from shrouded fluid-containing apparatus 22 to external components (e.g., framing members 24, ceiling joists, floor beams, and other load-bearing structures).

A shrouded end fitting 32 is disposed at an end of shrouded fluid-conducting apparatus 22. Preferably, a shrouded end fitting 32 is disposed at each end of each shrouded fluid-conducting apparatus 22. Shrouded end fittings 32 may be used to connect shrouded fluid-conducting apparatus 22 to an additional shrouded fluid-conducting apparatus 22 or shrouded flow meter assembly 20. Alternatively, shrouded fluid-conducting apparatus 22 may be connected by way of shrouded end fittings 32 to any one of a wide range of other fluid-conducting apparatus having end fittings mateable or engageable with shrouded end fittings 32, as would be obvious to one having ordinary skill in the art after becoming familiar with the teaching of the present invention. The shrouded end fittings 32 may also be used to hold or keep inner fluid-conducting conduit 26 substantially stationary with respect to outer conduit 28 and/or to transfer loads from inner and outer conduits 26 and 28 to an external component (e.g., ceiling joists, floor beams, and other load-bearing structures).

In the embodiment shown, shrouded fluid-conducting apparatus 22 uses flanged shrouded end fittings 32. It should be appreciated, however, that shrouded end fittings 32 can take a variety of forms. Additionally, it should be appreciated that shrouded fluid-conducting apparatus 22 is shown with reference to a specific embodiment although other embodiments can be employed. Possible other embodiments for shrouded fluid-conducting apparatus 22 and shrouded end fittings 32 are disclosed in U.S. Pat. No. 6,848,720, entitled "Shrouded Fluid-Conducting Apparatus," the disclosure of which is incorporated herein by reference. Additionally, further embodiments for shrouded fluid-conducting apparatus 22 and shrouded end fitting 32 are also disclosed in U.S. Patent App. Publication No. 2005/0120534A1, entitled "Shrouded Fluid-Conducting Apparatus," published Jun. 9, 2005, the disclosure of which is incorporated herein by reference.

Figure 2:
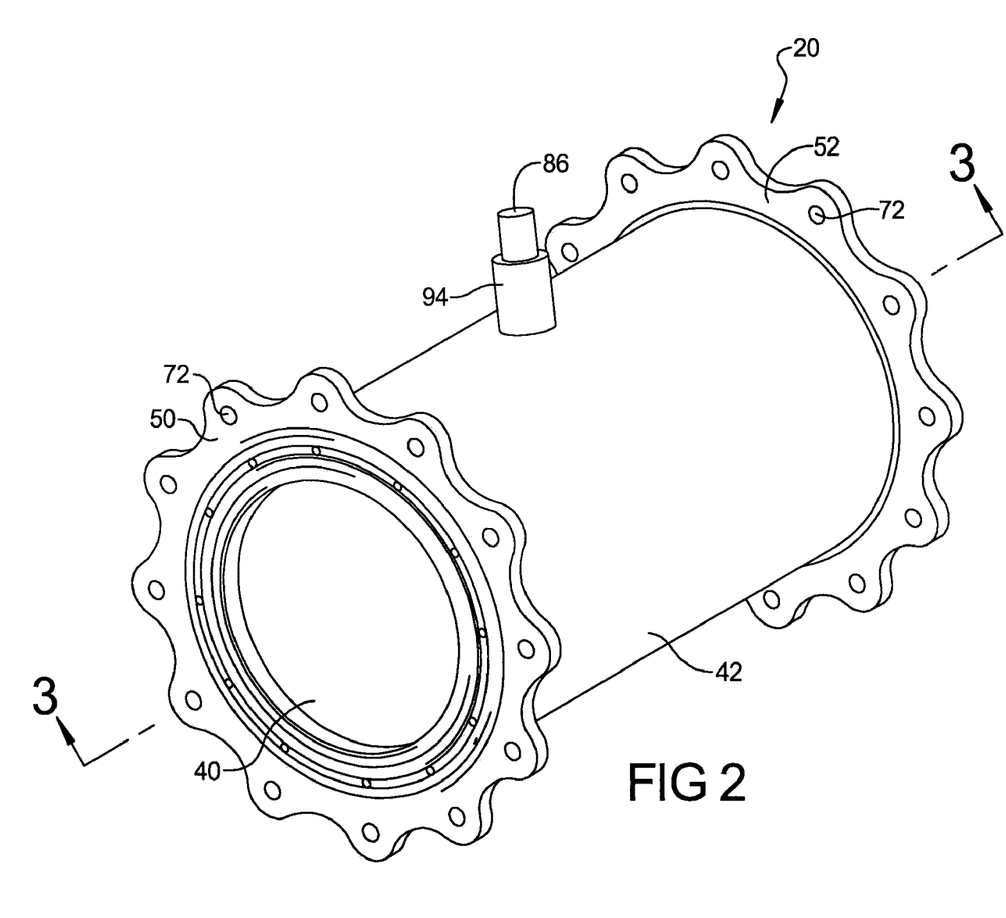
FIG. 2 is a perspective view of the shrouded flow meter assembly of FIG. 1.
Figure 3:
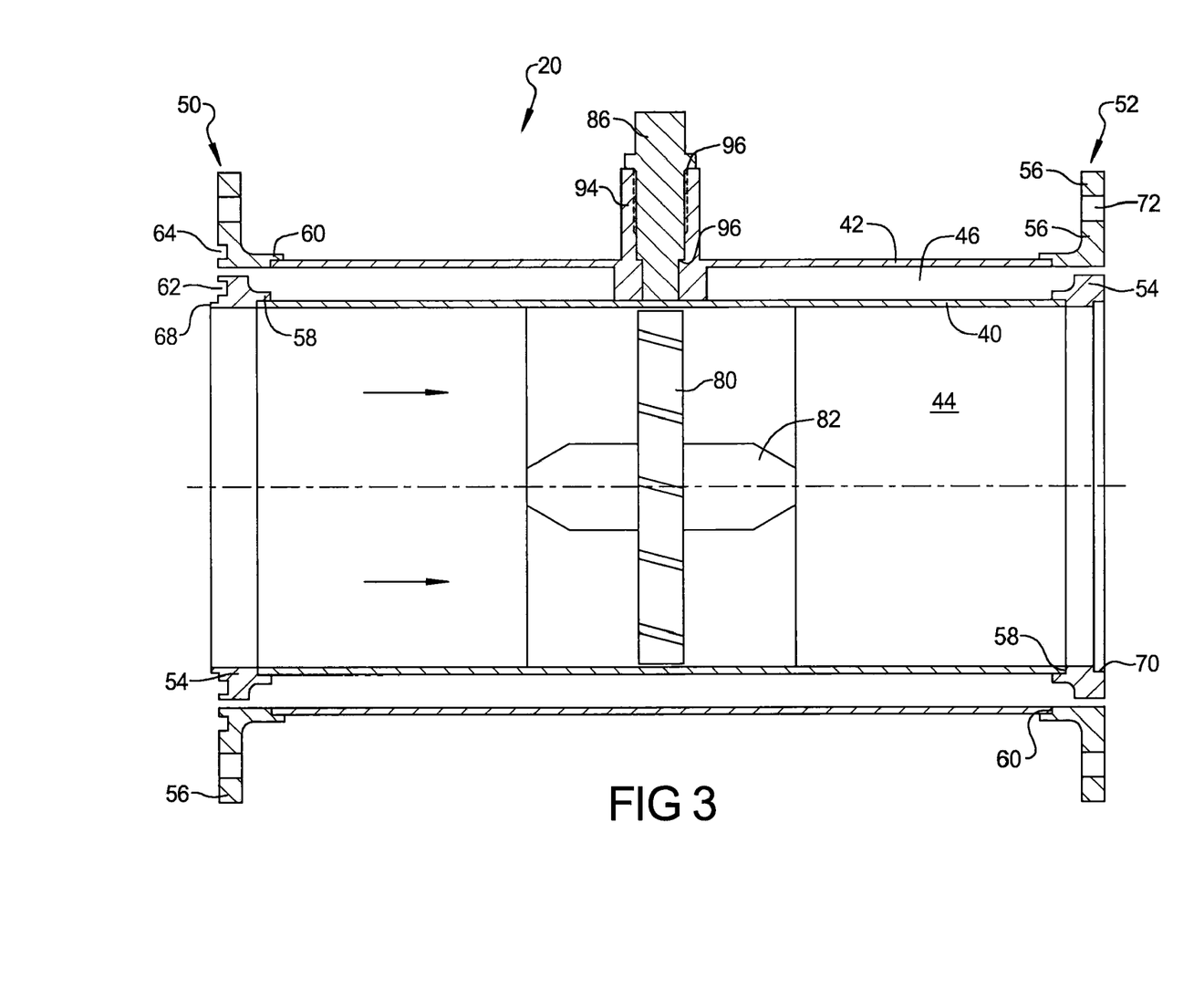
FIG. 3 is a cross-sectional view of the shrouded flow meter assembly along line 3-3 of FIG. 2.

Referring now to FIGS. 1, 2 and 3, shrouded flow meter assembly 20 includes an inner fluid-conducting conduit 40 disposed within and spaced apart from an outer conduit 42. Outer conduit 42 includes a lumen 46 (cavity or channel) that is sized to receive inner conduit 40. Inner conduit 40 includes a lumen (cavity or channel) 44 that allows for a fluid (e.g., gases and liquids) to flow through inner conduit 40. Outer conduit 42 shrouds inner conduit 40 to contain any fluid leaking from inner conduit 40 and prevents leaking fluid from reaching the compartment in which shrouded flow meter assembly 20 is being used. Accordingly, inner and outer conduits 40, 42 and/or any seals therein must both fail before a fluid being conducted through inner conduit 40 can reach the compartment or space in which shrouded flow meter assembly 20 is being used. Shrouded flow meter assembly 20 thus allows a fluid to be conducted through inner conduit 40 under a double failure condition.

Shrouded flow meter assembly 20 may include one or more support members (not shown) that support inner conduit 40 within outer conduit 42. Inner conduit 40 may be inclined to move or shift within outer conduit 42 while a fluid is being conducted through inner conduit 40. The support members can reduce and possibly prevent the movement of inner conduit 40 within outer conduit 42. In other words, the support members can hold or keep inner conduit 40 substantially stationary with respect to outer conduit 42. Additionally, the support members may also allow for loads to be transferred from shrouded flow meter assembly 20 to external components (e.g., framing member 24, ceiling joists, floor beams, and other load-bearing structures).

Shrouded end fittings 50, 52 are disposed on each end of shrouded flow meter assembly 20. End fittings 50, 52 are used to connect shrouded flow meter assembly 20 to shrouded fluid-conducting apparatus 22. End fittings 50, 52 are configured to engage with and provide a fluid-tight seal against end fittings 32 of shrouded fluid-containing apparatus 22. End fittings 50, 52 include inner and outer portions 54, 56 that engage with inner and outer conduits 40, 42 respectively.

Inner and outer portions 54, 56 may be provided with notches or weld sockets 58, 60 into which may be welded (e.g., fillet weld, butt weld, etc.) inner and outer conduits 40, 42, respectively. Additionally, inner and outer portions 54, 56 of end fitting 50 may each define a groove or a recess 62, 64, respectively, into which can be disposed a suitable sealing member, such as an O-ring, gasket or other type seal to provide a fluid-tight seal against a complementary end fitting, such as shrouded end fitting 32 of shrouded fluid-containing apparatus 22, to which it is to be secured.

To ensure proper alignment of shrouded end fittings 50, 52, end fittings 50, 52 may be shaped to interfit with another end fitting, such as end fitting 32, in a keyed arrangement or one relation alignment. For example, one end fitting 50, 52 may include an alignment tab or key (not shown) that is sized to fit within a notch or key way defined by the shrouded end fitting to which it is to be attached. Similarly, the other end fitting 50, 52 may include the notch or key way (not shown) that is configured to receive an alignment tab or key of a complementary end fitting to which it is to be secured. Or, for example, one of end fittings 50, 52, in this case end fitting 50, may, additionally or alternatively, include a radial protrusion (or index member) 68 that is disposed to engage a chamfered or beveled surface defined by the complementary shrouded end fitting to which it is to be secured. The other end fitting 50, 52, in this case end fitting 52, may, additionally or alternatively, include a chamfered or beveled surface 70 that is configured to engage with a radial protrusion on a complementary end fitting to which it is to be secured. Thus, each end fitting 50, 52 includes differing features to enable abutment to complementary fittings of other components. This arrangement enables other components, such as a shrouded fluid-conducting apparatus 22, to be removed from an existing system and replaced with a shrouded flow meter assembly 20. Additionally, if standardized lengths or sizes for these components are utilized, a shrouded flow meter assembly 20 can be easily and conveniently inserted into an existing system that contains one or more shrouded fluid-conducting apparatus 22 and/or to replace a different assembly having a similar configuration in a shrouded fluid-conducting system.

Outer portions 56 of end fittings 50, 52 include a plurality of openings 72 that are configured to align with openings in the outer portions of shrouded end fittings to which they are to be secured, such as shrouded end fitting 32. A plurality of fasteners 74 are used to secure abutting shrouded end fittings together, as shown in FIG. 1. It should be appreciated that while end fittings 50, 52 of shrouded flow meter assembly 20 and shrouded end fitting 32 of shrouded fluid-conducting apparatus 22 are shown as being flange-type fittings, other type fittings such as those disclosed in the above U.S. patent and patent applications incorporated by reference above, can be employed along with other end fittings that maintain the fluid integrity of the abutting inner and outer conduits.

Shrouded flow meter assembly 20 is operable to measure the flow of fluid through inner fluid-conducting conduit 40. To accomplish this, shrouded flow meter assembly 20 includes an impeller 80 attached to a shaft 82. Impeller 80 and shaft 82 are disposed within inner fluid-conducting conduit 40. Bearings (not shown) support shaft 82 within inner fluid-conducting conduit 40. Impeller 80 and shaft 82 rotate within inner fluid-conducting conduit 40 as a result of fluid flowing therethrough. A transducer 86 is disposed proximate impeller 80 with the wall of inner fluid-conducting conduit 40 therebetween. Transducer 86 detects rotation of impeller 80 via the blades of impeller 80 influencing the magnetic field of the magnetic pickup of transducer 86. Rotation of impeller 80 is detected as pulses per unit of time which are then equated to a flow rate for the fluid flowing through inner fluid-containing conduit 40. Transducer 86 is connected to a module 88 via a cable 90. Module 88 converts the pulses per unit of time to a flow rate for the fluid flowing through inner fluid-conducting conduit 40. The flow rate is communicated to the appropriate component of the system within which shrouded flow meter assembly 20 is utilized. To facilitate the detection of the rotation of impeller 80 by transducer 86, inner fluid-conducting conduit 40 is preferably made of a non-magnetic material, such as aluminum. The use of a non-magnetic material prevents interference with the detection of the magnetic pulses by transducer 86. If it is desired to use a magnetic material for inner fluid-conducting conduit 40, a window or portion of inner conduit 40 that is located between impeller 80 and transducer 86 can be made from a different material to avoid and/or limit interference with the detection of the magnetic pulses.

Transducer 86 is not in contact with the fluid flowing through inner fluid-conducting conduit 40. As such, the integrity of inner fluid-conducting conduit 40 is maintained. Transducer 86 is disposed within a fitting 94 in outer conduit 42. As such, transducer 86 is exposed to the space between inner and outer conduits 40, 42. To maintain the integrity of outer conduit 42, sealing members are used to seal transducer 86 to fitting 94. For example, O-rings 96 can be used to provide a fluid-tight seal between transducer 86 and fitting 94 to prevent the leakage of fluid between transducer 86 and fitting 94. Alternatively and/or additionally, other types of sealing members, such as gaskets, putty sealants, sealing tape, and the like may be used to form a fluid-tight seal between transducer 86 and fitting 94. Thus, the integrity of outer conduit 42 and that of inner conduit 40 is maintained in shrouded flow meter assembly 20.

Preferably, transducer 86 and fitting 94 include complementary threads that allow transducer 86 to be secured to fitting 94. The threaded engagement facilitates the removal and replacement of transducer 86 in the event of failure. It should be appreciated, however, that other types of engagement between transducer 86 and fitting 94 that allows transducer 86 to be removed therefrom and replaced, can be employed. Moreover, if desired, transducer 86 can be fixedly secured to fitting 94, although all the benefits of the present invention may not be realized. The maintaining of the integrity of inner fluid-conducting conduit 40 within shrouded flow meter assembly 20 enables transducer 86 to be replaced while fluid is present within inner fluid-conducting conduit 40 and without that fluid leaking therefrom.

Shrouded flow meter assembly 20 can be used in a variety of applications. For example, shrouded flow meter assembly 20 can be used in an aerial refueling system 110, shown in FIG. 4. Aerial refueling system 110 is situated on an aircraft 112 and enables aerial refueling of other aircraft. Aerial refueling system 110 includes left and right main fuel tanks 114, 116 that are located within respective left and right wings 118, 120 of aircraft 112. A central fuel tank 122 is disposed primarily within the fuselage 124 of aircraft 112 and extends partially into wings 118, 120. Fuel in left and right wing fuel tanks 114, 116 is selectively gravity fed to central fuel tank 122 via respective fluid flow lines 126, 128. Pumps 130 are operable to pump fuel from central fuel tank 122 to one of four different aerial refueling apparatuses. At the rear of aircraft 122 are an aerial boom 132 and an aerial hose 134. Aerial boom 132 and aerial hose 134 can be used to refill an aircraft from the rear of aircraft 112 depending upon the type of aircraft to be refueled and its fittings. The piping that interconnects pumps 130 with aerial boom 132 and aerial hose 134 travels through areas classified by the FAA as "ignition zones" and, accordingly, portions of that fuel line are shrouded and comprised of shrouded fluid-conducting apparatus 22. A shrouded flow meter assembly 20 is located within the system of shrouded fluid-conducting apparatus 22 and is used to meter the fluid flowing to aerial boom 132 and/or aerial hose 134. The portions of the fuel supply lines that feed aerial boom 132 and aerial hose 134 that are not classified by the FAA as "ignition zones" may utilize other fluid-conducting apparatuses.

Figure 4:
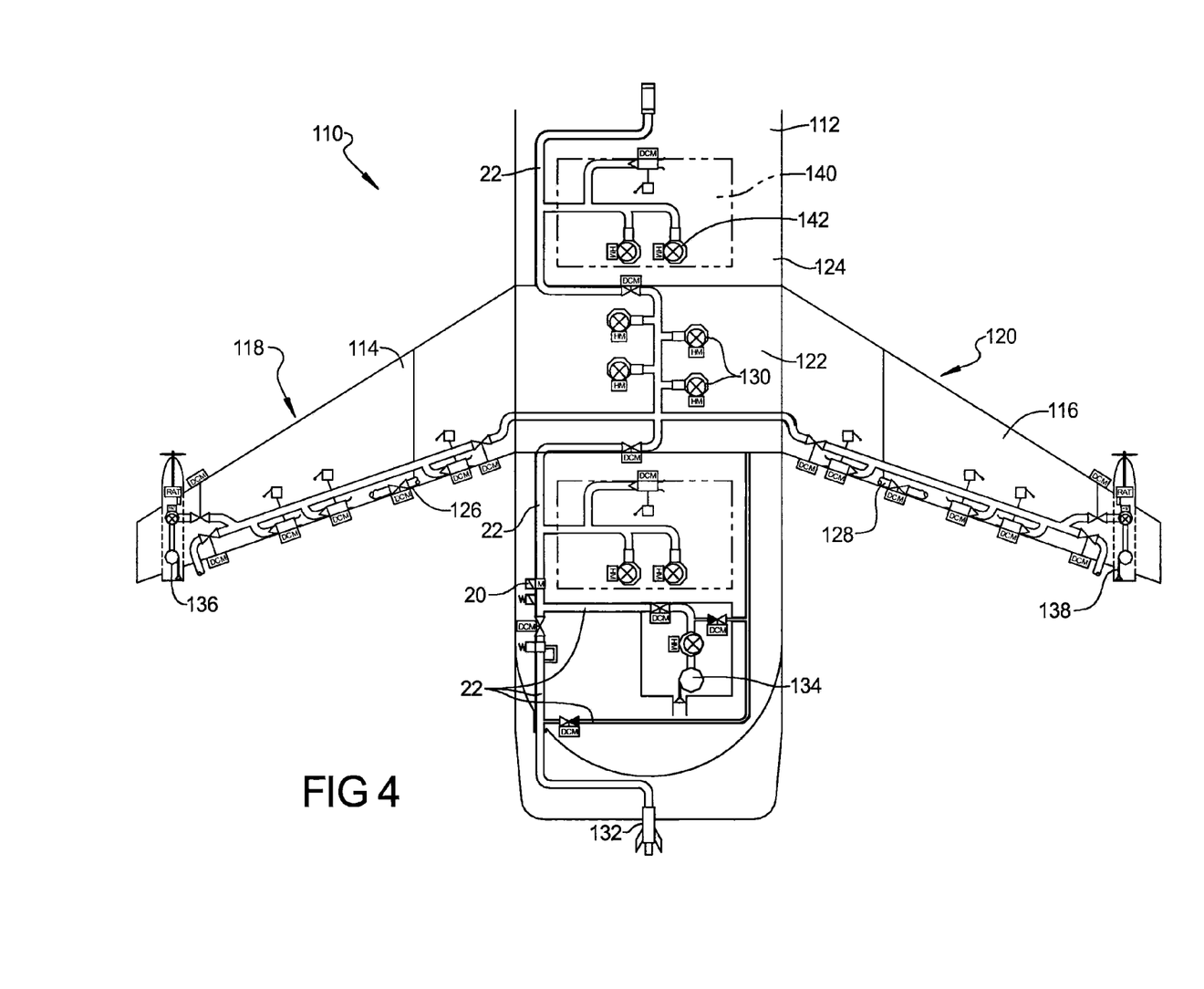
FIG. 4 is a schematic representation of an aircraft illustrating an environment within which the shrouded flow meter assembly of the present invention can be employed.

Pumps 130 are also operable to supply fuel to left and right aerial hoses 136, 138 that are disposed in the respective left and right wings 118, 120 of aircraft 112. The fuel flow lines supplying left and right aerial hoses 136, 138 do not travel through areas classified by the FAA as "ignition zones" and, accordingly, do not require the use of shrouded fluid-containing apparatus 22. Aerial refueling system 110 may also include an optional auxiliary fuel tank 140 and pumps 142. Auxiliary fuel tank 140 can be used to supply fuel to central fuel tank 122. The fuel lines between auxiliary fuel tank 140 and central fuel tank 122 travel through areas classified by the FAA as "ignition zones" and, accordingly, utilize shrouded fluid-containing apparatus 22.

While aerial refueling system 110 is shown as utilizing only a single shrouded flow meter assembly 20 according the principles of the present invention, it should be appreciated that aerial refueling system 110 can incorporate multiple shrouded flow meter assemblies 20, as needed, to measure the fluid flow through the various flow lines of aerial refueling system 110.

Aerial refueling system 110 is disclosed in more detail in U.S. patent application Ser. No. 11/313,190 entitled "Aerial Refueling System," filed on Dec. 20, 2005, mentioned above and the disclosure of which is incorporated herein by reference.

While the present invention has been disclosed with reference to a flow meter assembly, it should be appreciated that the principles of the present invention are applicable to other types of assemblies that can monitor and/or measure the fluid properties of a fluid flowing through a shrouded fluid conduit. For example, a temperature gauge transducer can be positioned on an exterior surface of inner fluid-conducting conduit 40 and sealed to fitting 94 of outer conduit 42. The temperature transducer would be operable to measure the temperature of the inner fluid-conducting conduit 40 which, presumably, may be at an equilibrium temperature with the fluid flowing therethrough. Another example is the use of densitometer, such as one utilizing radio fractometry, to determine the density of a fluid flowing through an inner fluid-conducting conduit 40. Furthermore, a non-contacting fuel level indicator or sensor may be utilized wherein the presence of fuel therein can be indicated by non-contacting means. Another example could be a non-discreet flow indicator that provides a signal indicative of whether a flow is greater or less than a predetermined value. It should be appreciated that other types of measuring devices can also be employed in a shrouded configuration beyond those discussed above.

Additionally, it should be appreciated that while shrouded flow meter assembly 20 is shown and described with reference to a particular embodiment, that changes and variations can be employed without departing from the spirit and scope of the present invention. Thus, while the preferred embodiment has been described, those skilled in the art will recognize modifications or variations which might be made without departing from the inventive concept. The examples illustrate the invention and are not intended to limit it. Therefore, the description and claims should be interpreted liberally with only such limitation as is necessary in view of the pertinent prior art.

What is claimed is:

1. A shrouded flow meter comprising:
    a fluid tight inner conduit operable to conduct a fluid therethrough, said inner conduit having an inlet and an outlet with respective inlet and outlet fittings;
    a fluid tight outer conduit disposed over said inner conduit with a space therebetween, said outer conduit having an inlet and an outlet with respective inlet and outlet fittings; and
    a detector attached to said outer conduit and extending from an exterior of said outer conduit, said detector operable to sense a signal indicative of a characteristic of a fluid in said inner conduit, said detector being isolated from direct contact with the fluid flowing through said inner conduit, and said detector being external to said interior of said inner conduit,
    wherein said inlet and outlet fittings of said inner conduit couple in a fluid-tight manner with end fittings of an inner conduit in other shrouded apparatuses, said inlet and outlet fittings of said outer conduit couple in a fluid tight manner with end fittings of an outer conduit in said other shrouded apparatuses, and said fluid-tight coupling of said inlet and outlet fittings of said inner conduit is independent of said fluid-tight coupling of said inlet and outlet fittings of said outer conduit.

2. The shrouded flow meter of claim 1, wherein said detector communicates with said space between said inner and outer conduits.

3. The shrouded flow meter of claim 1, further comprising a rotatable impeller in said inner conduit, said impeller rotating in response to fluid flowing through said inner conduit.

4. The shrouded flow meter of claim 1, wherein said detector can be removed from said outer conduit without compromising an integrity of said inner conduit.

5. The shrouded flow meter of claim 1, further comprising a seal member forming a fluid-tight seal between said detector and said outer conduit.

6. The shrouded flow meter of claim 5, wherein said seal member prevents fluid within said space from flowing out of said outer conduit through an interface between said detector and said outer conduit.

7. An aerial refueling system including the shrouded flow meter of claim 1.

8. The shrouded flow meter of claim 1, wherein said space between said inner and outer conduits communicates with a space between inner and outer conduits in an attached shrouded apparatus.

9. A method of determining a characteristic of fluid within an inner conduit of a shrouded fluid-conducting apparatus, the method comprising:
    (a) locating a detector proximate the inner conduit of the shrouded fluid-conducting apparatus while maintaining an integrity of the inner conduit, said detector being external to an interior cavity of the inner conduit and extending from an exterior of an outer conduit within which the inner conduit is disposed;
    (b) sensing a signal with said detector based on a fluid within the inner conduit;
    (c) converting said sensed signal into a characteristic of said fluid within the inner conduit; and (d) preventing said detector from contacting said fluid that flows within the inner conduit.

10. The method of claim 9, wherein (a) includes locating said detector in an outer conduit of the shrouded fluid-conducting apparatus.

11. The method of claim 10, wherein (a) includes locating said detector in said outer conduit and in communication with a space between said inner and outer conduits.

12. The method of claim 11, wherein (a) includes removeably locating said detector in said outer conduit such that said detector can be removed from said outer conduit while maintaining a fluid integrity of the inner conduit.

13. The method of claim 11, wherein (a) includes disposing a seal between said detector and said outer conduit such that fluid in said space between said inner and outer conduits cannot flow past said outer conduit through an interface between said detector and said outer conduit.

14. The method of claim 9, wherein (b) includes sensing a change in a magnetic field caused by fluid flowing through the inner conduit.

15. The method of claim 14, wherein (c) includes converting said sensed change in said magnetic field into a flow rate of said fluid flowing through the inner conduit.

16. The method of claim 14, further comprising rotating a magnetic field inducing member within said inner conduit with a fluid flowing through the inner conduit.

17. The method of claim 9, further comprising coupling inlet and outlet fittings of the inner conduit to end fittings of other shrouded apparatuses in a fluid-tight manner, and coupling inlet and outlet fittings of the outer conduit to end fittings of said other shrouded apparatuses in a fluid-tight manner independently of coupling the inlet and outlet fittings of the inner conduit.

* * * * *